(12) United States Patent
Rie et al.

(10) Patent No.: US 9,997,718 B2
(45) Date of Patent: Jun. 12, 2018

(54) ORGANIC PHOTOELECTRIC DEVICE IMAGE SENSOR AND ELECTRONIC DEVICE

(71) Applicant: Samsung Electronics Co., Ltd., Suwon-si, Gyeonggi-do (KR)

(72) Inventors: Sakurai Rie, Suwon-si (KR); Yong Wan Jin, Seoul (KR); Sung Young Yun, Suwon-si (KR); Gae Hwang Lee, Seongnam-si (KR); Kwang Hee Lee, Yongin-si (KR); Dong-Seok Leem, Hwaseong-si (KR); Bulliard Xavier, Seongnam-si (KR); Tadao Yagi, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days. days.

(21) Appl. No.: 15/008,076

(22) Filed: Jan. 27, 2016

(65) Prior Publication Data
US 2016/0301013 A1   Oct. 13, 2016

(30) Foreign Application Priority Data

Apr. 13, 2015 (KR) ................ 10-2015-0052019

(51) Int. Cl.
| | | |
|---|---|---|
| *C07D 495/22* | (2006.01) | |
| *C09K 11/06* | (2006.01) | |
| *H05B 33/14* | (2006.01) | |
| *H01L 51/50* | (2006.01) | |
| *H01L 51/00* | (2006.01) | |
| *H01L 27/30* | (2006.01) | |
| *H01L 51/42* | (2006.01) | |

(52) U.S. Cl.
CPC ........ *H01L 51/0071* (2013.01); *C07D 495/22* (2013.01); *C09K 11/06* (2013.01); *H01L 27/307* (2013.01); *H01L 51/0051* (2013.01); *H01L 51/0053* (2013.01); *H05B 33/14* (2013.01); *H01L 51/006* (2013.01); *H01L 51/0061* (2013.01); *H01L 51/0078* (2013.01); *H01L 51/4253* (2013.01); *H01L 2251/308* (2013.01)

(58) Field of Classification Search
CPC ...... C07D 495/22; C09K 11/06; H05B 33/14; H01L 51/5032; H01L 51/5064; H01L 51/0032; H01L 51/5296
USPC .............. 546/41; 548/405; 313/504; 257/40, 257/E51.05; 428/917
See application file for complete search history.

(56) References Cited

U.S. PATENT DOCUMENTS

| | | | | |
|---|---|---|---|---|
| 8,471,021 | B2 * | 6/2013 | Gao | C07D 495/22 257/40 |
| 9,252,371 | B1 * | 2/2016 | Yagi | H01L 51/008 |
| 9,502,473 | B2 * | 11/2016 | Lee | H01L 27/307 |
| 2012/0253045 | A1 | 10/2012 | Gao et al. | |
| 2016/0149132 | A1 * | 5/2016 | Lim | C07F 7/0818 257/40 |

FOREIGN PATENT DOCUMENTS

| | | | |
|---|---|---|---|
| CN | 101693719 A | 4/2010 | |
| CN | 101885732 A | 11/2010 | |
| CN | 102344456 A | 2/2012 | |
| CN | 102351879 A | 2/2012 | |
| CN | 103399072 A | 11/2013 | |
| CN | 103408570 A | 11/2013 | |
| WO | WO 9424612 A1 * | 10/1994 | ............... C07F 5/02 |
| WO | WO-2007012611 A1 | 2/2007 | |
| WO | WO-2013171518 A1 | 11/2013 | |
| WO | WO-2014022378 A2 | 2/2014 | |

OTHER PUBLICATIONS

Tan et al., J. Mater. Chem., 2011, 21, 18042.*
Hu et al. Tetrahedron Letters 54 (2013) 2271-2273.*
Luo et al. J. Mater. Chem. C, 2013, 1, 2688-2695.*
Houari et al. J. Phys. Chem. C 2013, 117, 21682-21691.*
Suraru, et al,,J. Org. Chem. 2013, 78, 5227-5238.*
Zhe Qi, et al."High-performance n-type organic thin-film phototransistors based on a core-expanded naphthalene diimide" Applied physics Letters, vol. 5 pp. 053301/1-053301/4 (2013).
Yuta Fukutomi, "Naphthodithiophenediimide (NDTI): Synthesis, Structure, and Applications", Journal of American Chemical Society, vol. 31, pp. 11445-11448 (2013).
Yunbin Hu, et al. "A facile synthesis of 2,3,6,7-tetrabromonaphthalene diimides toward new-extended naphthalene diimides", Tetrahedron Letters, vol. 54, pp. 2271-2273 (2013).
Jing Gao, et al. "Synthesis and Properties of Naphthobisbenzothiophene Diimides",Organic Letters, vol. 6, pp. 1366-1369, (2013).
Luxi Tan, et al. "New tetrathiafulvalene fused-naphthalene diimides for solution-processible and air-stable p-type and ambipolar organic semiconductors", Chemical Science vol. 3, pp. 2530-2541, (2012).
Fengjiao Zhang, et al. "Critical Role of Alkyl Chain Branching of Organic Semiconductors in Enabling Solution- Processed N-Channel Organic Thin-Film Transistors with Mobility of up to 3.50 cm2 V-1 s1", Journal of American Chemical Society, vol. 6. pp. 2338-2349, (2013).
Luxi Tan, et al. "New air-stable solution-processed organic n-type semiconductors based on sulfur-rich core-expanded naphthalene diimides", Journal of Materials Chemistry, vol. 21, pp. 18042-18048 (2011).
Yan Zhao, et al. "All-Solution-Processed, High- Performance n-Channel Organic Transistors and Circuits: Toward Low-Cost Ambient Electronics", Advanced Materials, vol. 21, pp. 2448-2453 (2011).
Yunbin Hu, et al. "Core-Expanded Naphthalene Diimides Fused with Sulfur Heterocycles and End-Capped with Electron-withdrawing Groups for Air-Stable Solution-Processed n-Channel Organic Thin Film Transistors", Chemistry of Materials, vol. 5, pp. 1204-1215 (2011).

(Continued)

*Primary Examiner* — Venkataraman Balasubramanian
(74) *Attorney, Agent, or Firm* — Harness, Dickey & Pierce, P.L.C.

(57) ABSTRACT

An organic photoelectric device includes a first electrode and a second electrode facing each other, and an active layer between the first electrode and the second electrode, the active layer including an n-type semiconductor compound represented by Chemical Formula 1 and a p-type semiconductor compound having selective light absorption in a green wavelength region of about 500 nm to about 600 nm.

21 Claims, 8 Drawing Sheets

(56) References Cited

OTHER PUBLICATIONS

Xike Gao, et al. "Core-Expanded Naphthalene Diimides Fused with 2-(1,3-Dithiol-2-Ylidene)Malonitrile Groups for High-Performance, Ambient-Stable, Solution-Processed n-Channel Organic Thin Film Transistors" Journal if the America Chemical Society, vol. 11, pp. 3697-3699, (2010).

Cheng Li, et al. "Synthesis and Properties of Heterocyclic Acene Diimides", Organic Letters, vol. 3, pp. 682-685, (2013).

Hukuto Seo et al. "Color Sensors with Three Vertically Stacked Organic Photodetectors". Japanese Journal of Applied Physics, vol. 46 No. 49. The Japan Society of Applied Physics. 2007. pp. L1240-L1242.

Satoshi Aihara et al. "Stacked Image Sensor With Green- and Red-Sensitive Organic Photoconductive Films Applying Zinc Oxide Thin-Film Transistors to a Signal Readout Circuit". IEEE Transactions on Electron Devices, vol. 56, No. 11. Nov. 2009. pp. 2570-2576.

Cornelia Roger et al. "Core-Tetrasubstituted Naphthalene Diimides: Synthesis, Optical Properties, and Redox Characteristics". American Chemical Society. JOC Article. Sep. 2007. pp. 8070-8075.

Prashant Kumar et al. "Hybrid n-GaN and polymer interfaces: Model systems for tunable photodiodes". Organic Electronics. 2013. p. 2818-2825.

Xin Chen et al. "New core-expanded naphthalene diimides with different functional groups for air-stable solution-processed organic n-type semiconductors". New Journal of Chemistry, vol. 37, No. 6. RSC Publishing. Jun. 2013. pp. 1633-1844.

Hewei Luo et al. "Solution-processed core-expanded naphthalene diimides toward organic n-type and amibipolar semiconductors". Journal of Materials Chemistry C. RCS Publishing. 2013. pp. 2688-2695.

\* cited by examiner

ORGANIC PHOTOELECTRIC DEVICE IMAGE SENSOR AND ELECTRONIC DEVICE

CROSS-REFERENCE TO RELATED APPLICATION

This application claims priority to and the benefit of Korean Patent Application No. 10-2015-0052019 filed in the Korean Intellectual Property Office on Apr. 13, 2015, the entire contents of which are incorporated herein by reference.

BACKGROUND

1. Field

Example embodiments relate to an organic photoelectric device, an image sensor, and an electronic device.

2. Description of the Related Art

A photoelectric device converts light into an electrical signal using photoelectric effects, and may include a photodiode and/or a phototransistor. The photoelectric device may be applied to an image sensor, a solar cell and/or an organic light emitting diode.

An image sensor including a photodiode requires relatively high resolution and thus a relatively small pixel. At present, a silicon photodiode is widely used, but may have a problem of deteriorated sensitivity since the silicon photodiode has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide an organic photoelectric device being capable of selectively absorbing light in a green wavelength region and improving efficiency.

Example embodiments also provide an image sensor including the organic photoelectric device and an electronic device.

According to example embodiments, an organic photoelectric device includes a first electrode and a second electrode facing each other, and an active layer between the first electrode and the second electrode, the active layer including an n-type semiconductor compound represented by Chemical Formula 1 and a p-type semiconductor compound having selective light absorption in a green wavelength region of about 500 nm to about 600 nm.

[Chemical Formula 1]

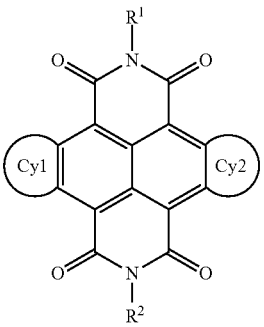

In Chemical Formula 1,
each of $R^1$ and $R^2$ are independently one of a substituted or unsubstituted $C_1$ to $C_6$ linear or branched alkyl group, a substituted or unsubstituted phenyl group, a substituted or unsubstituted 4-membered to 6-membered heteroaryl group, a substituted or unsubstituted $C_3$ to $C_6$ cycloalkyl group, and a substituted or unsubstituted 3-membered to 6-membered heterocycloalkyl group, and
each of Cy1 and Cy2 are independently selected from Chemical Formulae 2-1 to 2-5.

[Chemical Formulae 2-1 to 2-5]

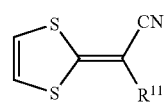 (2-1)

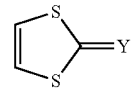 (2-2)

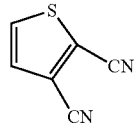 (2-3)

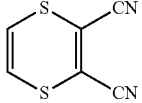 (2-4)

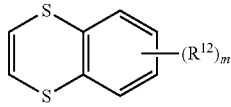 (2-5)

In Chemical Formula 2-1,
$R^{11}$ is one of hydrogen, a cyano group (CN), a carboxyl group (—COOH), an ester group (—COOR, wherein R is a $C_1$ to $C_6$ linear or branched alkyl group), a phenyl group, and a phenyl group substituted with a $C_1$ to $C_6$ alkyl group,
in Chemical Formula 2-2,
Y is one of O, S, and NR (wherein R is one of hydrogen, a cyano group (CN), and a $C_1$ to $C_6$ linear or branched alkyl group), and
in Chemical Formula 2-5,
$R^{12}$ is one of hydrogen, a cyano group (CN), a carboxyl group (—COOH), and an ester group (—COOR, wherein R is a $C_1$ to $C_6$ linear or branched alkyl group), and
m is an integer of 0 to 1.

In Chemical Formula 1, Cy1 and Cy2 may be the same or different.

The n-type semiconductor compound represented by Chemical Formula 1 may have 6 to 10 rings.

Each of the $R^1$ and $R^2$ may independently be one of a $C_1$ to $C_6$ linear or branched alkyl group substituted with an electron withdrawing group, a phenyl group substituted with an electron withdrawing group, a 4-membered to 6-membered heteroaryl group substituted with an electron withdrawing group, a $C_3$ to $C_6$ cycloalkyl group substituted with an electron withdrawing group, and a 3-membered to 6-membered heterocycloalkyl group substituted with an electron withdrawing group. Herein, the electron withdrawing group may be a cyano group or a halide group.

The p-type semiconductor compound may be a compound represented by Chemical Formula 3.

[Chemical Formula 3]

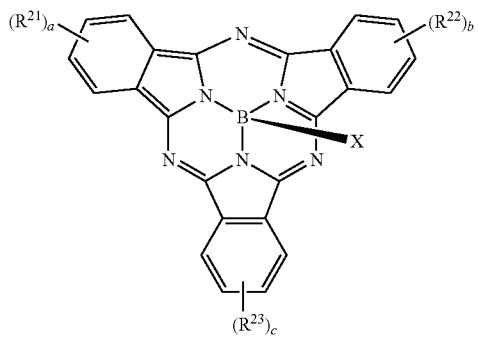

In Chemical Formula 3, each of $R^{21}$ to $R^{23}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halide group, a halogen-containing group, and a combination thereof, each of a, b, and c are independently an integer ranging from 1 to 3, and X is one of a halide group, for example —F or —Cl, and —Si($R^a$)($R^b$)($R^c$), wherein each of the $R^a$, $R^b$, and $R^c$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group, and a combination thereof.

In Chemical Formula 3, $R^{21}$ to $R^{23}$ may be an electron donating functional group including one of a substituted or unsubstituted $C_1$ to $C_{30}$ alkyl group, a substituted or unsubstituted $C_6$ to $C_{30}$ aryl group, and a substituted or unsubstituted $C_3$ to $C_{30}$ heteroaryl group.

The p-type semiconductor compound may be a compound represented by Chemical Formula 4.

[Chemical Formula 4]

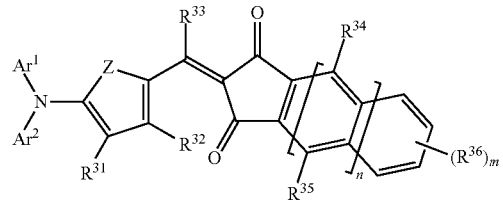

In Chemical Formula 4,

Z is one of Se, Te, S(=O), S(=O)$_2$, and SiR$^a$R$^b$ (wherein R$^a$ and R$^b$ are one of hydrogen and a $C_1$ to $C_{10}$ alkyl group), each of $Ar^1$ and $Ar^2$ are one of a substituted or unsubstituted $C_6$ to $C_{30}$ aryl group and a substituted or unsubstituted $C_4$ to $C_{30}$ heteroaryl group, each of $R^{31}$ to $R^{36}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halide, and a cyano group (CN), m is an integer ranging from 0 to 4, and n is 0 or 1.

The compound represented by Chemical Formula 4 may have 5 to 7 aromatic rings.

$Ar^1$ and $Ar^2$ may be a substituted or unsubstituted $C_6$ to $C_{20}$ aryl group.

At least one of the $Ar^1$ and $Ar^2$ may be one of a naphthyl group and an anthracenyl group.

The active layer of the organic photoelectric device may have a maximum absorption wavelength ($\lambda_{max}$) of about 500 nm to about 600 nm.

The active layer of the organic photoelectric device may show a light absorption curve having a full width at half maximum (FWHM) of about 50 nm to about 140 nm.

The active layer may include an intrinsic layer including the n-type semiconductor compound and the p-type semiconductor compound.

The active layer may further include at least one of a p-type layer on one side of the intrinsic layer and an n-type layer on the other side of the intrinsic layer.

Example embodiments provide an image sensor including the organic photoelectric device.

The image sensor may include a semiconductor substrate integrated with a plurality of first photo-sensing devices configured to sense light in a blue wavelength region and a plurality of second photo-sensing devices configured to sense light in a red wavelength region, wherein the organic photoelectric device is on the semiconductor substrate and configured to selectively absorb light in a green wavelength region.

The plurality of first photo-sensing devices and the plurality of second photo-sensing devices may be stacked in a vertical direction on the semiconductor substrate.

The image sensor may further include a color filter layer between the semiconductor substrate and the organic photoelectric device, and the color filter layer including a blue filter configured to selectively absorb light in a blue wavelength region and a red filter configured to selectively absorb light in a red wavelength region.

The organic photoelectric device may be a green photoelectric device, and the green photoelectric device, a blue photoelectric device configured to selectively absorb light in a blue wavelength region, and a red photoelectric device configured to selectively absorb light in a red wavelength region may be stacked.

Example embodiments also provide an electronic device including the image sensor.

DETAILED DESCRIPTION

Figure 1:
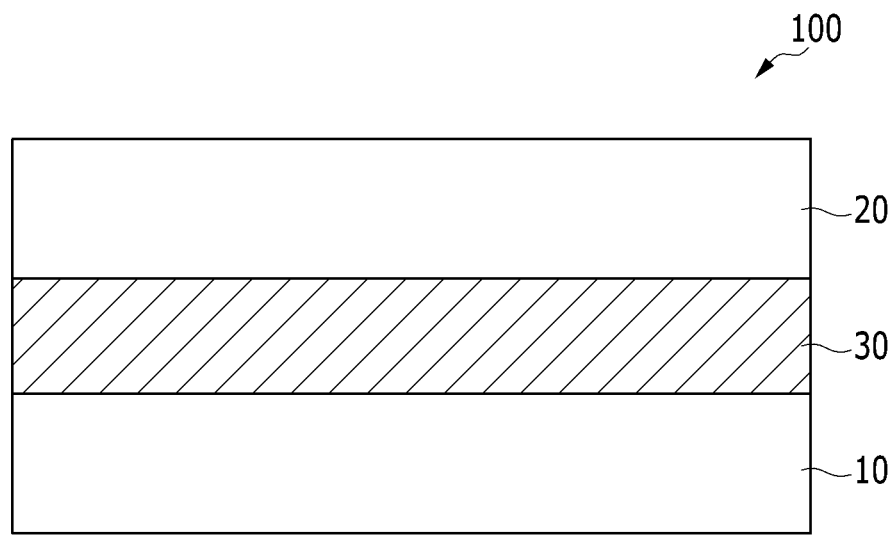
FIG. 1 is a cross-sectional view showing an organic photoelectric device according to example embodiments.

Example embodiments of the present inventive concepts will hereinafter be described in detail, and may be more easily performed by those who have common knowledge in the related art. However, this disclosure may be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when specific definition is not otherwise provided, the term "substituted" refers to one substituted with a substituent selected from a halide group (—F, —Br, —Cl, or —I), a hydroxy group, a nitro group, a cyano group, an amino group (—NRR', wherein R and R' are a $C_1$ to $C_6$ linear or branched alkyl group, an ester group (—COOR, wherein R is a $C_1$ to $C_6$ linear or branched alkyl group), a $C_1$ to $C_{10}$ alkyl group, a $C_2$ to $C_{10}$ alkenyl group, a $C_2$ to $C_{10}$ alkynyl group, a $C_1$ to $C_{10}$ alkoxy group, and a combination thereof, instead of hydrogen of a compound or a functional group.

As used herein, when specific definition is not otherwise provided, the term "hetero" refers to one including 1 to 3 heteroatoms selected from N, O, S, and P.

As used herein, when a definition is not otherwise provided, the "halide group" refers to —F, —Cl, —Br, or —I, and the "halogen-containing group" refers to a group where at least one hydrogen is replaced by —F, —Cl, —Br, or —I. For example, the haloalkyl group refers to an alkyl group where at least one hydrogen is replaced by —F, —Cl, —Br, or —I. Examples of the haloalkyl group may be a fluoroalkyl group, for example a perfluoroalkyl group.

Hereinafter, an organic photoelectric device according to example embodiments is described referring to drawings.

FIG. 1 is a cross-sectional view showing an organic photoelectric device according to example embodiments.

Referring to FIG. 1, an organic photoelectric according to example embodiments includes a first electrode 10 and a second electrode 20, and an active layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a monolayer or multilayer. When one of the first electrode 10 and the second electrode 20 is a non-light-transmitting electrode, it may be made of, for example, an opaque conductor (e.g., aluminum (Al)).

The active layer 30 includes a p-type semiconductor and an n-type semiconductor to form a pn junction, and absorbs external light to generate excitons and then separates the generated excitons into holes and electrons.

The active layer 30 includes an n-type semiconductor compound represented by Chemical Formula 1 and a p-type semiconductor compound having selective light absorption in a green wavelength region of about 500 nm to about 600 nm.

[Chemical Formula 1]

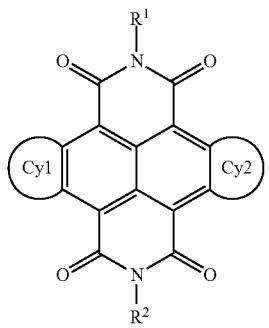

In Chemical Formula 1,
each of $R^1$ and $R^2$ are independently one of a substituted or unsubstituted $C_1$ to $C_6$ linear or branched alkyl group, a substituted or unsubstituted phenyl group, a substituted or unsubstituted 4-membered to 6-membered heteroaryl group, a substituted or unsubstituted $C_3$ to $C_6$ cycloalkyl group, and a substituted or unsubstituted 3-membered to 6-membered heterocycloalkyl group, and
each of Cy1 and Cy2 are independently one of Chemical Formulae 2-1 to 2-5.

[Chemical Formulae 2-1- to 2-5]

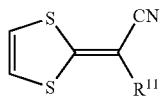 (2-1)

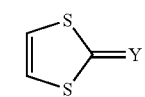 (2-2)

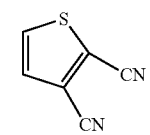 (2-3)

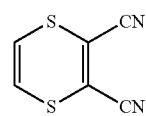 (2-4)

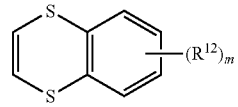 (2-5)

In Chemical Formula 2-1,
$R^{11}$ is one of hydrogen, a cyano group (CN), a carboxyl group (—COOH), an ester group (—COOR, wherein R is one of a $C_1$ to $C_6$ linear or branched alkyl group), a phenyl group, and a phenyl group substituted with a $C_1$ to $C_6$ alkyl group,
in Chemical Formula 2-2,
Y is one of O, S, and NR (wherein R is selected from hydrogen, a cyano group (CN), and a $C_1$ to $C_6$ linear or branched alkyl group), and
in Chemical Formula 2-5,
$R^{12}$ is one of hydrogen, a cyano group (CN), a carboxyl group (—COOH) and an ester group (—COOR, wherein R is a $C_1$ to $C_6$ linear or branched alkyl group), and
m is an integer of 0 to 1.

The n-type semiconductor compound represented by Chemical Formula 1 includes naphthalene diimide as a core, and a naphthyl group of the core is fused with an S-containing ring (Cy1 and Cy2) and provides the compound with a conjugation structure. The compound having this conjugation structure may absorb light having a long wavelength compared with naphthalene diimide including no S-containing ring.

In addition, the S-containing ring has electron-withdrawing properties, and may selectively absorb light in a green wavelength region ranging from about 500 nm to about 600 nm.

In Chemical Formula 1, Cy1 and Cy2 may be the same or different. When the Cy1 and Cy2 are different, the absorption wavelength range may be minutely adjusted.

The n-type semiconductor compound represented by Chemical Formula 1 may have 6 to 10 rings, for example 6 to 8 rings. Herein, the rings may indicate fused rings forming a conjugation structure. When the number of the rings is greater than 10, the maximum absorption wavelength of a compound moves toward red, and thus selective green light absorption of the compound is deteriorated. In addition, when the number of the rings is less than 6, the maximum absorption wavelength of a compound moves toward blue, and thus, selective green light absorption of the compound is deteriorated. In addition, the green wavelength selectivity of the n-type semiconductor compound may be improved by providing an appropriate conjugation length.

In Chemical Formula 1, each of $R^1$ and $R^2$ may independently be one of a substituted or unsubstituted $C_1$ to $C_6$ linear or branched alkyl group, a substituted or unsubstituted phenyl group, a substituted or unsubstituted 4-membered to 6-membered heteroaryl group, a substituted or unsubstituted $C_3$ to $C_6$ cycloalkyl group, and a substituted or unsubstituted 3-membered to 6-membered heterocycloalkyl group, and thereby the n-type semiconductor compound represented by Chemical Formula 1 may be desirably used for a deposition process. For example, when a long alkyl group (e.g., n-octyl or 2-hexyldecyl) is present in the $R^1$ and $R^2$ as shown in Comparative Synthesis Examples 1 and 2, the decomposition temperature of a compound becomes too high, and thus a deposition process may not be performed. Accordingly, a substituent of a substituted $C_1$ to $C_6$ linear or branched alkyl group, a substituted phenyl group, a substituted 4-membered to 6-membered heteroaryl group, a substituted $C_3$ to $C_6$ cycloalkyl group, and a substituted 3-membered to 6-membered heterocycloalkyl group may be one of a halide group (—F, —Br, —Cl, or —I), a hydroxy group, a nitro group, a cyano group, a $C_1$ to $C_4$ alkyl group, a $C_2$ to $C_4$ alkenyl group, a $C_2$ to $C_4$ alkynyl group, and a $C_1$ to $C_4$ alkoxy group.

In addition, each of the $R^1$ and $R^2$ may independently be one of a $C_1$ to $C_6$ linear or branched alkyl group substituted with an electron withdrawing group, a phenyl group substituted with an electron withdrawing group, a 4-membered to 6-membered heteroaryl group substituted with an electron withdrawing group, a $C_3$ to $C_6$ cycloalkyl group substituted with an electron withdrawing group, and a 3-membered to 6-membered heterocycloalkyl group substituted with an electron withdrawing group. Herein, the electron-withdrawing group may be a cyano group or a halide group.

The n-type semiconductor compound represented by Chemical Formula 1 may have a HOMO level ranging from about 5.8 to about 7.0 eV and a LUMO level ranging from about 3.8 to about 5.0 eV. When the HOMO and LUMO levels are respectively within the ranges, the semiconductor compound may effectively absorb light in a green wavelength region, and thus have high external quantum efficiency (EQE), improving photoelectric conversion efficiency.

On the other hand, a method of forming a thin film may be formed in a vacuum deposition method and a solution method. The vacuum deposition method may include very few impurities in the film and improve performance of a device. In addition, the solution method has a problem in completely removing a solvent and a problem of deteriorating a life-span or performance of a device due to remaining solvent, which is not found in the vacuum deposition method. Accordingly, the n-type semiconductor compound represented by Chemical Formula 1 has a structure that is appropriate for a vacuum deposition process as well as excellent selective light absorption in a green wavelength region.

The n-type semiconductor compound represented by Chemical Formula 1 may have a molecular weight ranging from about 300 to about 900, and specifically, about 350 to about 750. When the molecular weight is within the range, the compound is effectively prevented or inhibited from undergoing thermal decomposition as well as from developing crystallinity during formation of a thin film in the deposition method.

The n-type semiconductor compound represented by Chemical Formula 1 may have a decomposition temperature (Td) of greater than or equal to about 250° C., and specifically, greater than or equal to about 300° C. Herein, the decomposition temperature indicates a temperature at which the weight of a compound starts to decrease according to an exothermic reaction under an inert atmosphere during thermogravimetric analysis. For example, the decomposition temperature indicates a temperature at which the weight of the compound is reduced by about 1% according to an exothermic reaction when the temperature is increased at 10° C./min under the inert atmosphere during the thermogravimetric analysis.

Accordingly, a compound having a molecular weight within the range and the aforementioned decomposition temperature may adopt the vacuum deposition method to manufacture a device and provide an organic photoelectric device having excellent photoelectric conversion performance.

The n-type semiconductor compound represented by Chemical Formula 1 may selectively absorb light in a green wavelength region, and thus the active layer 30 including the compound may selectively absorb light in a green wavelength region having a maximum absorption wavelength ($\lambda_{max}$) ranging from about 500 nm to about 600 nm, for example, about 520 nm to about 580 nm.

The active layer 30 may show a light absorption curve having a relatively narrow full width at half maximum (FWHM) of about 50 nm to about 140 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased.

The active layer 30 further includes a p-type semiconductor compound in order to form a pn junction with the n-type semiconductor compound represented by Chemical Formula 1.

The p-type semiconductor compound may be a compound represented by Chemical Formula 3.

[Chemical Formula 3]

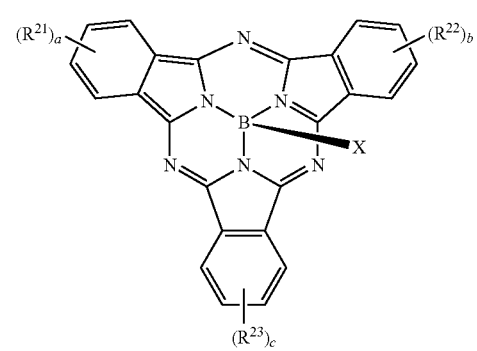

In Chemical Formula 3, each of $R^{21}$ to $R^{23}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halide group, a halogen-containing group, and a combination thereof, each of a, b, and c are independently an integer ranging from 1 to 3, and X is one of a halide group, for example, —F or —Cl, and —Si($R^a$)($R^b$)($R^c$), wherein each of the $R^a$, $R^b$, and $R^c$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group, and a combination thereof.

In Chemical Formula 3, $R^{21}$ to $R^{23}$ may be electron donating functional groups one of a substituted or unsubstituted $C_1$ to $C_{30}$ alkyl group, a substituted or unsubstituted $C_6$ to $C_{30}$ aryl group, and a substituted or unsubstituted $C_3$ to $C_{30}$ heteroaryl group.

The p-type semiconductor compound may be a compound represented by Chemical Formula 4.

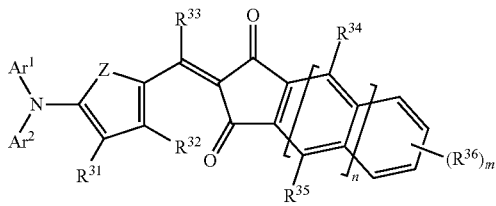

[Chemical Formula 4]

In Chemical Formula 4,

Z is one of Se, Te, S(=O), S(=O)$_2$, and SiR$^a$R$^b$ (wherein R$^a$ and R$^b$ are one of hydrogen and a C$_1$ to C$_{10}$ alkyl group), each of Ar$^1$ and Ar$^2$ are independently one of a substituted or unsubstituted C$_6$ to C$_{30}$ aryl group and a substituted or unsubstituted C$_4$ to C$_{30}$ heteroaryl group, each of R$^{31}$ to R$^{36}$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halide, and a cyano group (CN), m is an integer ranging from 0 to 4, and n is 0 or 1.

The compound represented by Chemical Formula 4 may have 5 to 7 aromatic rings. Herein, the aromatic ring refers to a 5-membered or 6-membered ring that provides a ring conjugation structure.

Ar$^1$ and Ar$^2$ may be a substituted or unsubstituted C$_6$ to C$_{20}$ aryl group.

At least one of the Ar$^1$ and Ar$^2$ may be a naphthyl group or an anthracenyl group.

At least one of the Ar$^1$ and Ar$^2$ may be one of a naphthyl group and an anthracenyl group, and in example embodiments, one of Ar$^1$ and Ar$^2$ may desirably be a naphthyl group. When at least one of the Ar$^1$ and Ar$^2$ is a naphthyl group or an anthracenyl group, aggregation among molecules in a film state may be suppressed by reducing intermolecular interaction among the molecules. Herein, absorption selectivity in a green wavelength may be improved. When the Ar$^1$ and Ar$^2$ are not aromatic groups but are alkyl groups or are fused each other and form an N-containing cycloalkyl group, the compound has a planer structure and an excessively wide full width at half maximum (FWHM) in a light absorption curve.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the n-type semiconductor compound represented by Chemical Formula 1 and the p-type semiconductor compound in a thickness ratio of about 1:100 to about 100:1. The compounds may be included in a thickness ratio ranging from about 1:50 to about 50:1 within the range, for example, about 1:10 to about 10:1, and for another example, about 1:1. When the compounds have a thickness ratio within the range, an exciton may be effectively produced and a pn junction may be effectively formed.

The n-type layer may include the n-type semiconductor compound represented by Chemical Formula 1, and the p-type layer may include the p-type semiconductor compound one of the semiconductor compound represented by Chemical Formula 3, the semiconductor compound represented by Chemical Formula 4, and a combination thereof.

The active layer 30 may have a thickness of about 1 nm to about 500 nm, for example, about 5 nm to about 300 nm. When the active layer 30 has a thickness within the range, the active layer may effectively absorb light, effectively separate holes from electrons, and deliver them, thereby effectively improving photoelectronic conversion efficiency. An optimal thickness of a thin film may be, for example, determined by an absorption coefficient of the active layer 30, and may be, for example, a thickness being capable of absorbing at least about 70% or more of light, for example, about 80% or more of light, and for another example, about 90% of light.

In the organic photoelectric device 100, when light enters from the first electrode 10 and/or second electrode 20, and when the active layer 30 absorbs light having a predetermined or given wavelength region, excitons may be produced from the inside. The excitons are separated into holes and electrons in the active layer 30, the separated holes are transported to an anode that is one of the first electrode 10 and the second electrode 20, and the separated electrons are transported to the cathode that is the other of and the first electrode 10 and the second electrode 20 so as to flow a current in the organic photoelectric device.

Hereinafter, an organic photoelectric device according to example embodiments is described with reference to FIG. 2.

Figure 2:
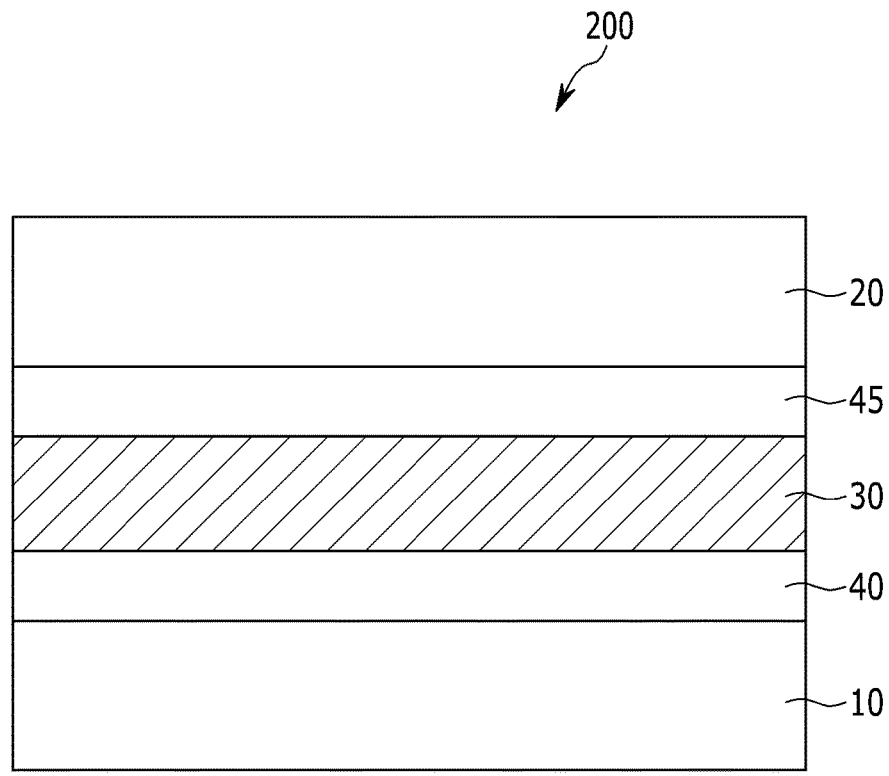
FIG. 2 is a cross-sectional view showing an organic photoelectric device according to example embodiments.

FIG. 2 is a cross-sectional view showing an organic photoelectric device according to example embodiments.

Referring to FIG. 2, an organic photoelectric device 200 according to example embodiments includes a first electrode 10 and a second electrode 20 facing each other, and an active layer 30 interposed between the first electrode 10 and the second electrode 20, like the example embodiments illustrated in FIG. 1.

However, the organic photoelectric device 200 according to example embodiments further includes charge auxiliary layers 40 and 45 between the first electrode 10 and the active layer 30, and the second electrode 20 and the active layer 30, unlike the example embodiments illustrated in FIG. 1. The charge auxiliary layers 40 and 45 may facilitate the transfer of holes and electrons separated from the active layer 30, so as to increase efficiency.

The charge auxiliary layers 40 and 45 may be at least one of a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, or nickel oxide).

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example, a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
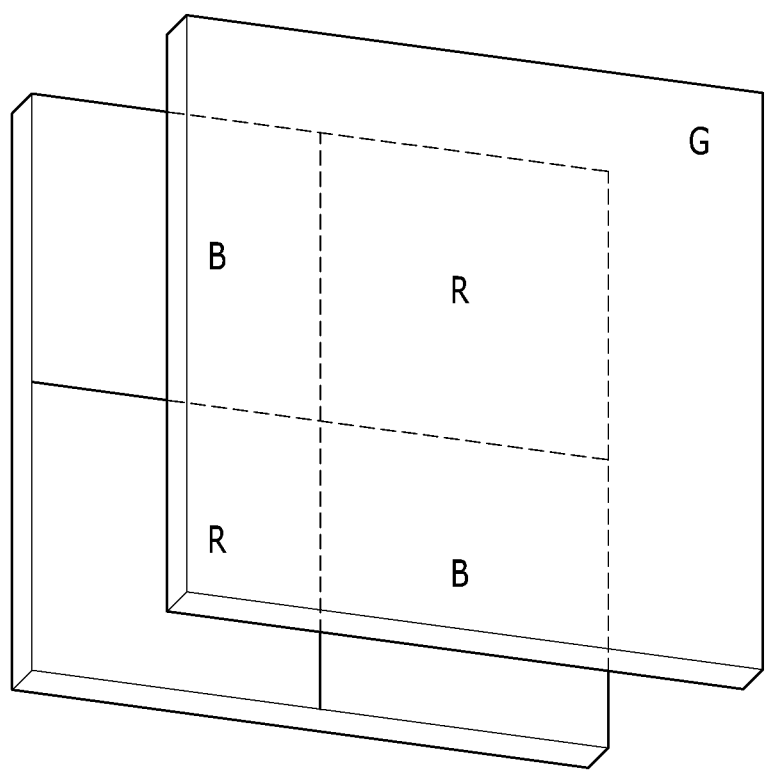
FIG. 3 is a schematic view showing an organic CMOS image sensor according to example embodiments.
Figure 4:
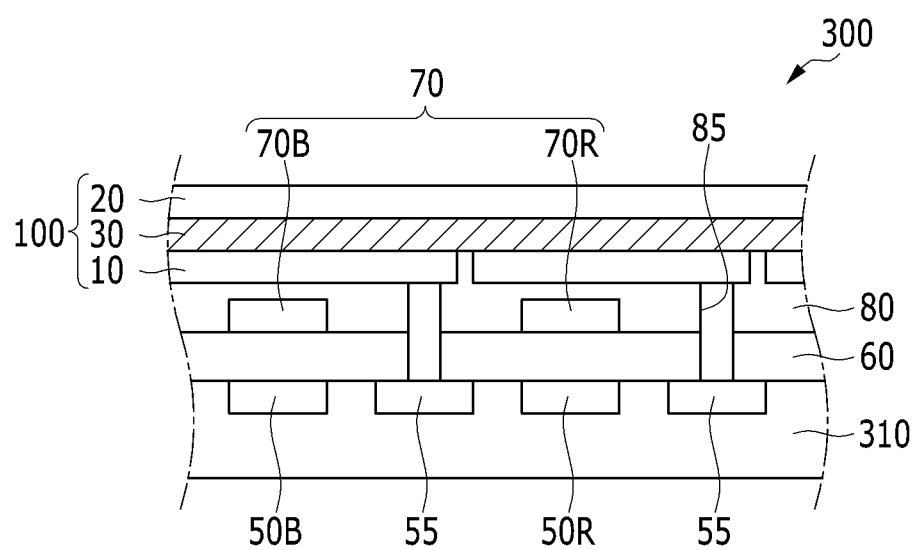
FIG. 4 is a cross-sectional view showing the organic CMOS image sensor of FIG. 3.

FIG. 3 is a schematic view of an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing devices 50B and 50R, the transmission transistor (not shown), and the charge storage 55. The photo-sensing devices 50B and 50R may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel, and the charge storage 55 may be included in a green pixel.

The photo-sensing devices 50B and 50R sense light, the information sensed by the photo-sensing devices may be transferred by the transmission transistor, the charge storage 55 is electrically connected with the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material (e.g., a silicon oxide and/or a silicon nitride), or a low dielectric constant (low K) material (e.g., SiC, SiCOH, SiCO, and SiOF). The lower insulation layer 60 has a trench exposing the charge storage device 55. The trench may be filled with fillers.

The color filter layer 70 is formed on the lower insulation layer 60. The color filter layer 70 includes a blue filter 70B formed in the blue pixel and a red filter 70R filled in the red pixel. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectronically converted, while the light in the rest of the wavelength region passes through first electrode 10 and may be sensed in the photo-sensing devices 50B and 50R.

An organic photoelectric device including the n-type semiconductor compound represented by Chemical Formula 1 and the p-type semiconductor compound shows excellent selective green absorption, and thus may be usefully applied to an image sensor having a stacking structure shown in FIGS. 3 and 4. As described above, the organic photoelectric device selectively absorbing light in a green wavelength region is stacked, and thereby a size of an image sensor may be decreased and a down-sized image sensor may be realized.

Figure 5:
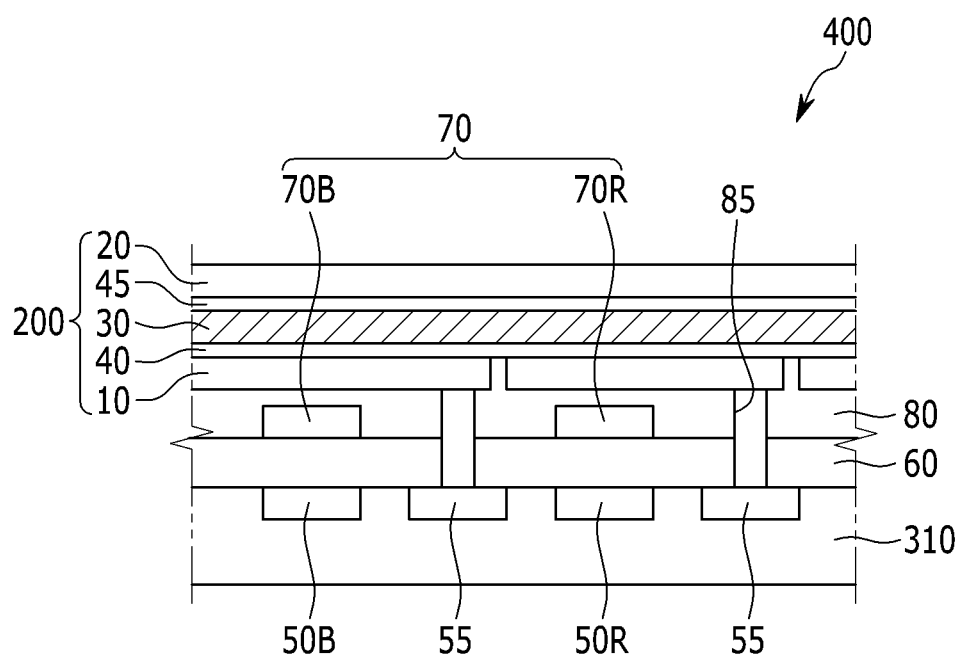
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
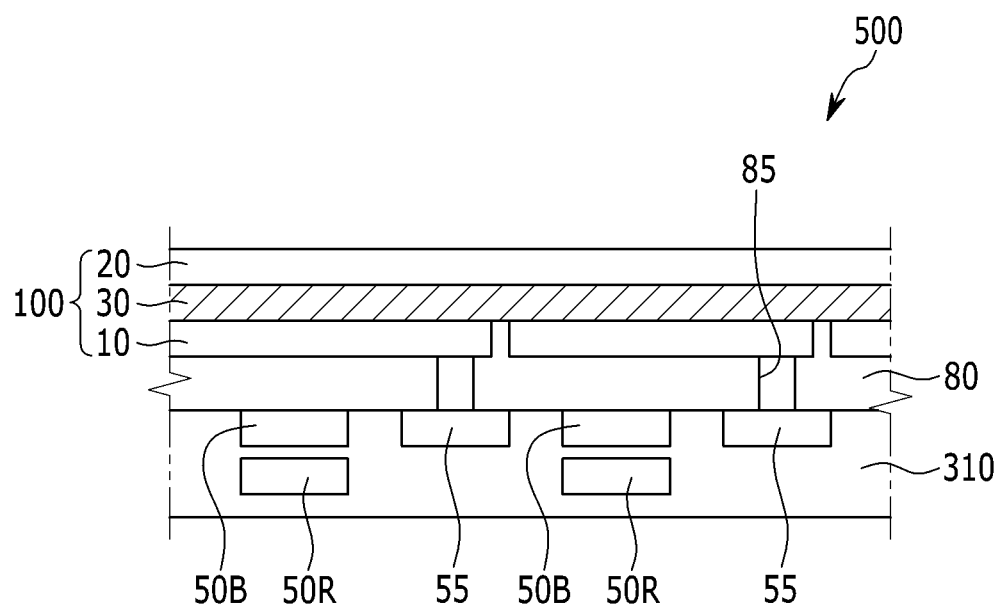
FIG. 6 is a schematic cross-sectional view showing the organic CMOS image sensor according to example embodiments.

FIG. 6 is a schematic cross-sectional view showing an organic CMOS image sensor according to example embodiments.

Referring to FIG. 6, the organic CMOS image sensor 500 according to example embodiments includes a semiconductor substrate 310 integrated with photo-sensing devices 50B and 50R, a transmission transistor (not shown), a charge storage 55, an insulation layer 80, and an organic photoelectric device 100, like the example embodiments illustrated in FIG. 5.

However, the organic CMOS image sensor 500 according to example embodiments includes the blue photo-sensing device 50B and the red photo-sensing device 50R that are stacked and does not include a color filter layer 70, unlike the example embodiments illustrated in FIG. 5. The blue photo-sensing device 50B and the red photo-sensing device 50R are electrically connected with the charge storage, and the information of the charge storage device 55 may be transferred by the transmission transistor (not shown). The blue photo-sensing device 50B and the red photo-sensing device 50R may selectively absorb light in each wavelength region depending on a stack depth.

An organic photoelectric device including the n-type semiconductor compound represented by Chemical Formula 1 and the p-type semiconductor compound shows excellent selective green light absorption, and thus may be usefully applied to an image sensor having a stacking structure shown in FIG. 6. As described above, the organic photoelectric device selectively absorbing light in a green wavelength region is stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption of light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
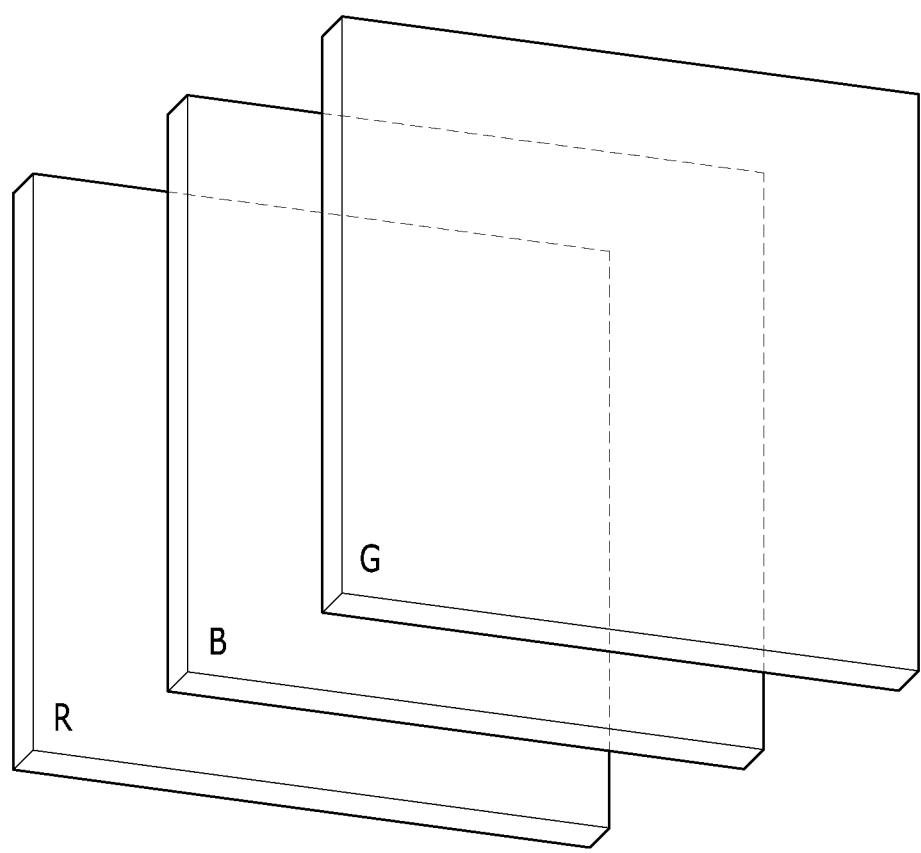
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor 500 according to example embodiments includes a green photoelectric device (G) selectively absorbing light in a green wavelength region, a blue photoelectric device (B) selectively absorbing light in a blue wavelength region, and a red photoelectric device (R) selectively absorbing light in a red wavelength region that are stacked.

In the drawing, the red photoelectric device (R), the blue photoelectric device (B) and the green photoelectric device (G) are sequentially stacked, but the stack order may be changed without limitation.

The green photoelectric device (G) may be the above organic photoelectric device 100, the blue photoelectric device (B) may include electrodes facing each other and an active layer interposed therebetween and including an organic material selectively absorbing light in a blue wavelength region, and the red photoelectric device (R) may include electrodes facing each other and an active layer interposed therebetween and including an organic material selectively absorbing light in a red wavelength region.

As described above, the organic photoelectric device (G) selectively absorbing light in a green wavelength region, the organic photoelectric device (B) selectively absorbing light in a blue wavelength region and the organic photoelectric device (R) selectively absorbing light in a red wavelength region are stacked, and thereby a size of an image sensor may be decreased and a down-sized image sensor may be realized.

The image sensor may be applied to various electronic devices, for example a mobile phone, a digital camera, and the like, but is not limited thereto.

Hereinafter, the present disclosure is illustrated in more detail with reference to examples. However, these are examples, and the present disclosure is not limited thereto.

SYNTHESIS EXAMPLES

Synthesis Example 1

A compound including a functional group provided in Table 1 is synthesized according to the following Reaction Scheme 1.

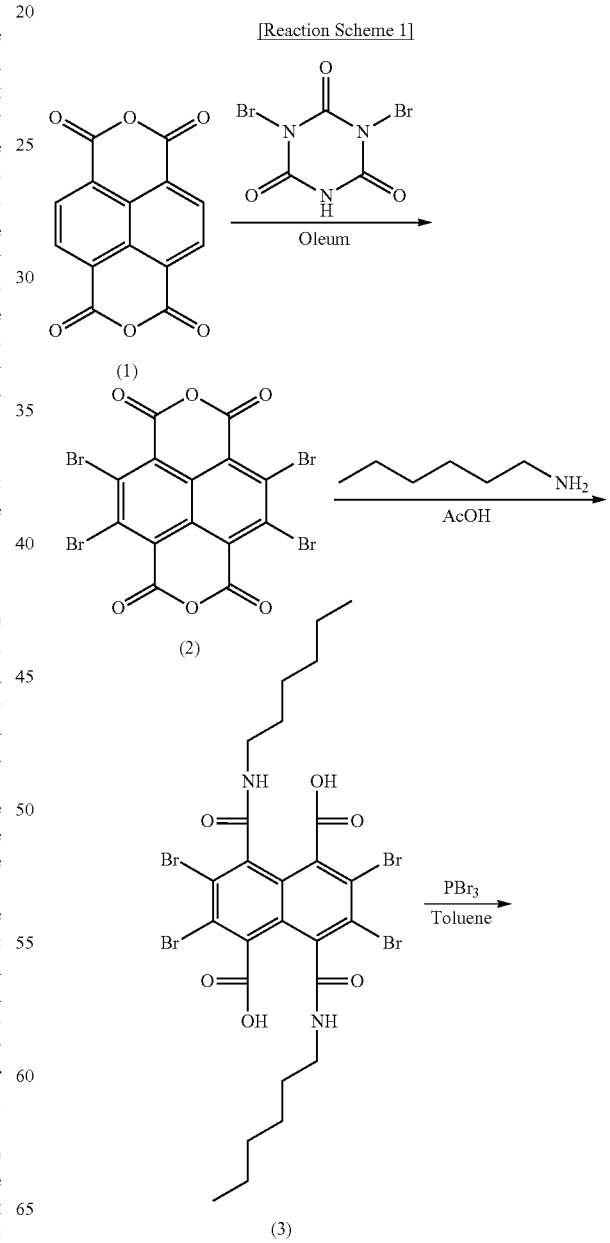

-continued

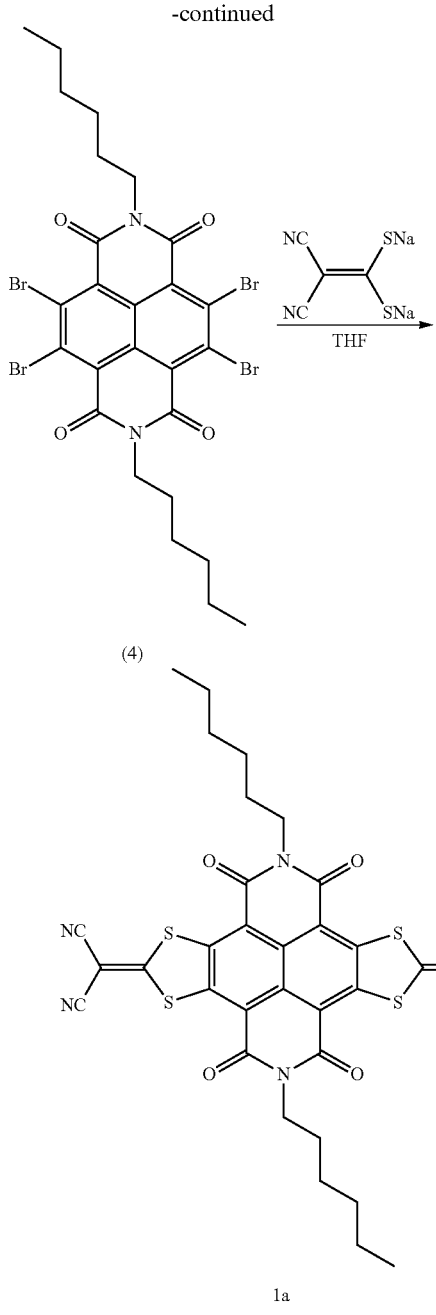

(4)

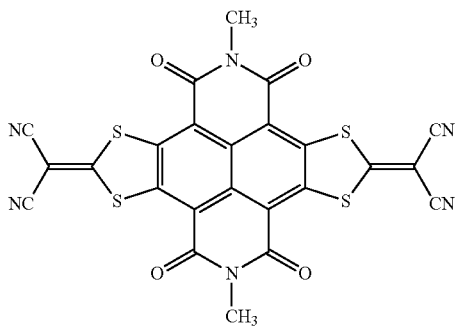

1a

A compound 2 is synthesized according to a method provided in, J. Org. Chem. 2007, 72, P. 8074. 1 g (1.7 mmol) of the compound 2 is suspended in 17 ml of acetic acid, 6.8 mmol of n-hexylamine is added thereto, and the mixture is heated at 120° C. for 25 minutes. Then, the resultant is cooled down to 24° C., and 130 ml of water is added thereto. The obtained precipitate is cleaned with water, obtaining a compound 3. The compound 3 is dissolved in 44 ml of dehydrated toluene, 30.66 ml (7.0 mmol) of PBr is added thereto, and the mixture is heated and refluxed for 12 hours under an argon atmosphere. Then, the resultant is cooled down to 24° C., 50 ml of water is added thereto, and the mixture is extracted with toluene. An organic layer obtained therefrom is then purified through silica gel column chromatography (development solvent: toluene:hexane=a volume ratio of 3:2), obtaining a compound 4. 0.2 mmol of the compound 4 and 0.06 mmol of sodium 1,1-dicyanoethene-2,2-thiolate are dissolved in 30 ml of tetrahydrofuran (THF), and the solution is heated and agitated at 50° C. for 1 and a half hours. Then, a solid obtained by taking a precipitate therefrom is cleaned in THF, obtaining 92 mg of a compound represented by Chemical Formula 1a (yield: 55%).

$^1$H NMR (300 MHz, CDCl$_3$) δ 4.17 (t, 4H), 1.75-1.73 (m, 4H), 1.39-1.37 (m, 12H), 0.92 (t, 6H)

Synthesis Example 2

A compound represented by Chemical Formula 1b (62 mg, yield: 55%) is obtained according to the same method as Synthesis Example 1, except for using methylamine instead of the n-hexylamine.

$^1$H NMR (300 MHz, CDCl$_3$) δ 4.01 (s, 6H)

[Chemical Formula 1b]

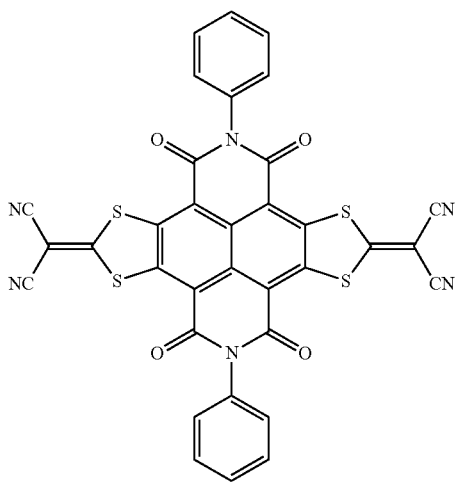

Synthesis Example 3

A compound (93 mg, yield: 67%) represented by Chemical Formula 1c is obtained according to the same method as Synthesis Example 1, except for using aniline instead of the n-hexylamine.

$^1$H NMR (300 MHz, DMSO-d$_6$) δ 7.50 (t, 4H), 7.41 (t, 2H), 7.33 (d, 4H)

[Chemical Formula 1c]

Synthesis Example 4

A compound represented by Chemical Formula 1d (85 mg, yield: 60%) is obtained according to the same method as Synthesis Example 1, except for using dimercaptomaleonitrile disodium instead of the sodium 1,1-dicyanoethene-2,2-thiolate.

$^1$H NMR (300 MHz, CDCl$_3$) δ 4.18 (t, 4H), 1.75-1.73 (m, 4H), 1.39-1.38 (m, 12H), 0.92 (t, 6H)

[Chemical Formula 1d]

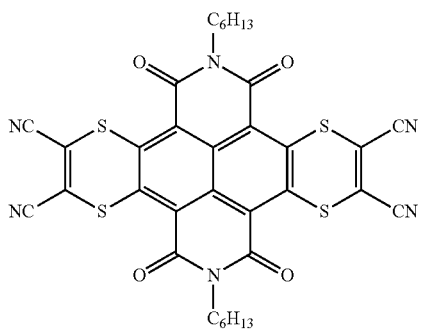

Synthesis Example 5

0.1 mmol of the compound represented by Chemical Formula 1a according to Synthesis Example 4 is dissolved in 20 ml of propionic acid, 0.8 ml of hydrogen peroxide is added thereto, and the mixture is heated and agitated at 120° C. for 3 hours. The resultant is cooled down to 24° C., and 20 ml of methanol is added thereto, obtaining a solid compound represented by Chemical Formula 1e (46 mg, yield: 70%).

$^1$H NMR (300 MHz, CDCl$_3$) δ 4.18 (t, 4H), 1.74-1.72 (m, 4H), 1.40-1.37 (m, 12H), 0.92 (t, 6H)

[Chemical Formula 1e]

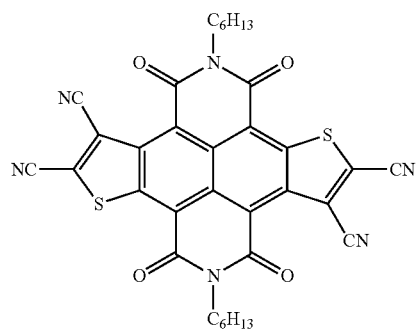

Synthesis Example 6

A compound represented by Chemical Formula 1f (106 mg, yield: 68%) is obtained according to the same method as Synthesis Example 1, except for using 2-cyano-3,3-dimercapto-2-propenoic acid methylester instead of the sodium 1,1-dicyanoethene-2,2-thiolate.

$^1$H NMR (300 MHz, CDCl$_3$) δ 4.17 (t, 4H), 3.81 (s, 4H), 1.75-1.73 (m, 4H), 1.38-1.37 (m, 12H), 0.91 (t, 6H)

[Chemical Formula 1f]

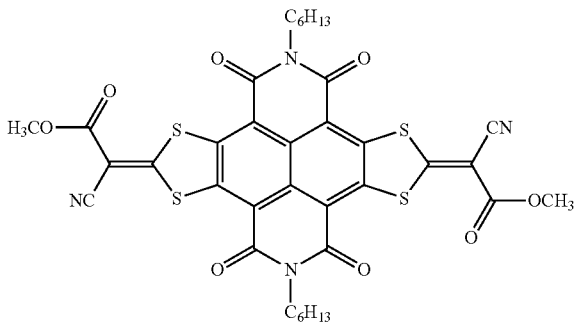

Synthesis Example 7

A compound represented by Chemical Formula 1g (82 mg, yield: 62%) is obtained according to the same method as Synthesis Example 1, except for using cyanoiminodithiocarbonic acid instead of the sodium 1,1-dicyanoethene-2,2-thiolate.

$^1$H NMR (300 MHz, CDCl$_3$) δ 4.19 (t, 4H), 1.75-1.73 (m, 4H), 1.38-1.36 (m, 12H), 0.93 (t, 6H)

[Chemical Formula 1g]

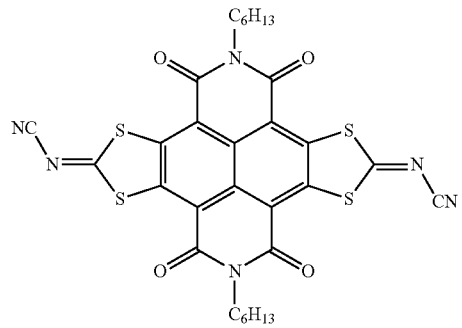

Synthesis Example 8

A compound represented by Chemical Formula 1h (139 mg, yield: 98%) is obtained according to the same method as Synthesis Example 1, except for using 1,2-benzendithiol instead of the sodium 1,1-dicyanoethene-2,2-thiolate.

$^1$H NMR (300 MHz, CDCl$_3$) δ 7.37-7.35 (m, 4H), 7.21-7.19 (m, 4H), 4.18 (t, 4H), 1.75-1.73 (m, 4H), 1.39-1.38 (m, 12H), 0.92 (t, 6H)

[Chemical Formula 1h]

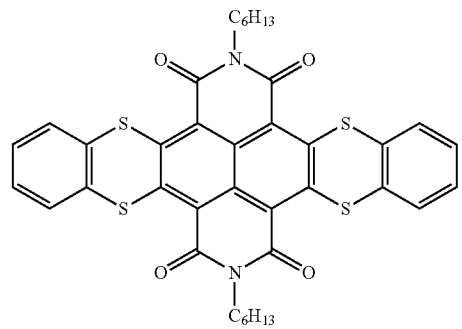

Synthesis Example 9

A compound represented by Chemical Formula 1i (50 mg, yield: 35%) is obtained according to the same method as Synthesis Example 1, except for using the sodium 1,1-dicyanoethene-2,2-thiolate in an amount of 0.3 mmol instead of 0.6 mmol and 0.3 mmol of disodium dimercaptomaleonitrile.

$^1$H NMR (300 MHz, CDCl$_3$) δ 4.18 (t, 4H), 1.73 (m, 4H), 1.38 (m, 12H), 0.92 (t, 6H)

[Chemical Formula 1i]

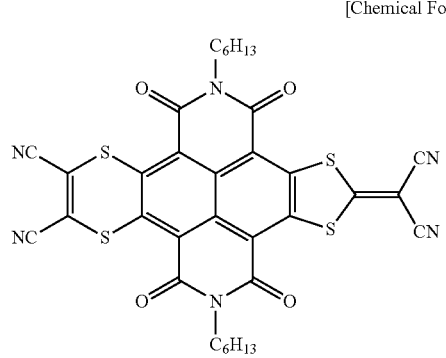

Synthesis Example 10

0.1 mmol of the compound represented by Chemical Formula 1i according to Synthesis Example 9 is dissolved in 20 ml of propionic acid, 0.8 ml of hydrogen peroxide is added thereto, and the mixture is heated and agitated at 120° C. for 3 hours. The resultant is cooled down to 24° C., and 20 ml of methanol is added thereto, obtaining a solid compound represented by Chemical Formula 1j (50 mg, yield: 73%).

$^1$H NMR (300 MHz, CDCl$_3$) δ 4.18 (t, 4H), 1.73 (m, 4H), 1.38 (m, 12H), 0.92 (t, 6H)

[Chemical Formula 1j]

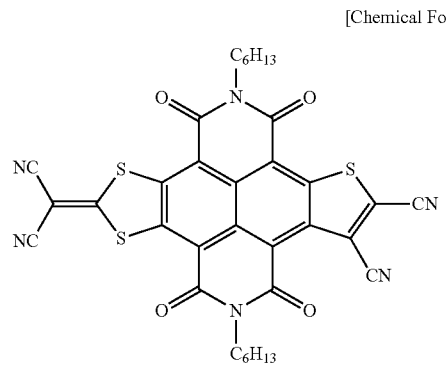

Comparative Synthesis Example 1

A compound represented by Chemical Formula 1k (92 mg, yield: 60%) is obtained according to the same method as Synthesis Example 1, except for using n-octylamine instead of the n-hexylamine.

$^1$H NMR (300 MHz, CDCl$_3$) δ 4.30 (t, 4H), 1.80 (m, 4H), 1.25-1.30 (m, 20H), 0.86 (t, 6H)

[Chemical Formula 1k]

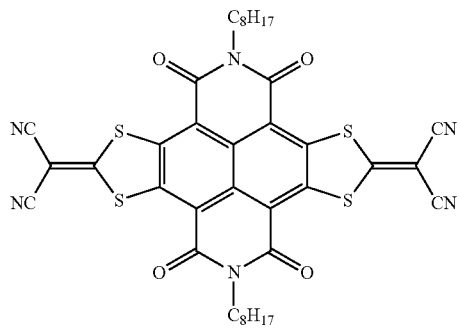

Comparative Synthesis Example 2

A compound represented by Chemical Formula 1l (106 mg, yield: 52%) is obtained according to the same method as Synthesis Example 1, except for using 2-hexyldecylamine instead of the n-hexylamine.

$^1$H NMR (300 MHz, CDCl$_3$) δ 4.22 (d, 4H), 2.00 (m, 2H), 1.25 (m, 48H), 0.85-0.87 (m, 12H)

[Chemical Formula 1l]

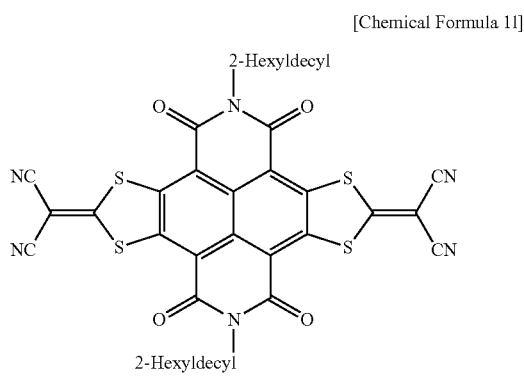

Deposition Temperatures of Compounds According to Synthesis Examples 1 to 10 and Comparative Synthesis Examples 1 and 2

When each compound according to Synthesis Examples 1 to 10 and Comparative Synthesis Examples 1 and 2 is deposited at a rate of 1 Å/s, a temperature of a crucible containing the compound is measured and provided in the following Table 1.

TABLE 1

| | Deposition temperature (° C.) |
|---|---|
| Synthesis Example 1 | 350 |
| Synthesis Example 2 | 305 |
| Synthesis Example 3 | 390 |
| Synthesis Example 4 | 310 |
| Synthesis Example 5 | 320 |
| Synthesis Example 6 | 335 |
| Synthesis Example 7 | 345 |
| Synthesis Example 8 | 360 |
| Synthesis Example 9 | 345 |
| Synthesis Example 10 | 355 |
| Comparative Synthesis Example 1 | >450 (deposition is impossible) |
| Comparative Synthesis Example 2 | >450 (deposition is impossible) |

Deposition Temperatures and Light Absorption Characteristics of Compounds According to Synthesis Examples 1 to 10 and Comparative Synthesis Examples 1 and 2

Light absorption characteristics of the compounds in a solution state and in a thin film state are measured.

The light absorption characteristics of the compounds according to Synthesis Examples 1 to 10 and Comparative Synthesis Examples 1 and 2 in a solution state are measured by respectively dissolving them in $CH_2Cl_2$ to have a concentration of $1.0 \times 10^{-5}$ mol/L. The maximum absorption wavelength of the compounds in a solution state is calculated by using a UV-2450 UV-Visible Spectrophotometer (Shimadzu Co.).

Light absorption characteristics in a thin film are obtained by thermally depositing each compound according to Synthesis Examples 1 to 10 and Comparative Synthesis Examples 1 and 2 and a p-type semiconductor compound in a volume ratio of 1:1 under high vacuum ($<10^{-7}$ Torr) at a rate of 0.5-1.0 Å/s to respectively form a 70 nm-thick thin film and measuring its maximum absorption wavelength in a thin film with a UV-2450 UV-Visible Spectrophotometer (Shimadzu Co.). The results are provided in Table 2.

The p-type semiconductor compound may include SubPcCl (a compound represented by Chemical Formula 3, wherein $R^{21}$ to $R^{23}$ are hydrogen, and X is Cl), a compound (2-((5-(naphthalen-1-yl(phenyl)amino)selenophen-2-yl) methylene)-1H-indene-1,3(2H)-dione) represented by Chemical Formula 4-1, or a compound represented by Chemical Formula 4-2.

[Chemical Formula 4-1]

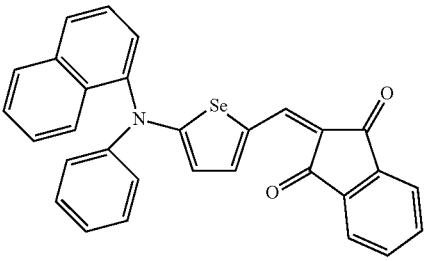

[Chemical Formula 4-2]

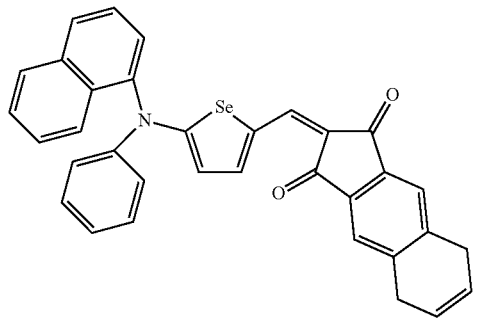

TABLE 2

|  | Solution state | | Thin film state | | | | | |
|---|---|---|---|---|---|---|---|---|
|  | | | SubPcCl | | Chemical Formula 4-1 | | Chemical Formula 4-2 | |
|  | $\lambda_{max}$ (nm) | FWHM (nm) | $\lambda_{max}$ (nm) | FWHM (nm) | $\lambda_{max}$ (nm) | FWHM (nm) | $\lambda_{max}$ (nm) | FWHM (nm) |
| Synthesis Example 1 | 574 | 38 | 580 | 135 | 538 | 120 | 564 | 129 |
| Synthesis Example 2 | 572 | 35 | 578 | 133 | 535 | 117 | 565 | 130 |
| Synthesis Example 3 | 583 | 34 | 590 | 120 | 536 | 113 | 561 | 124 |
| Synthesis Example 4 | 547 | 98 | 585 | 130 | 540 | 125 | 567 | 133 |
| Synthesis Example 5 | 545 | 40 | 588 | 135 | 537 | 127 | 570 | 134 |
| Synthesis Example 6 | 581 | 34 | 586 | 132 | 541 | 130 | 572 | 136 |
| Synthesis Example 7 | 511 | 20 | 556 | 120 | 538 | 109 | 562 | 124 |
| Synthesis Example 8 | 584 | 85 | 587 | 132 | 539 | 125 | 565 | 128 |
| Synthesis Example 9 | 557 | 75 | 590 | 133 | 533 | 128 | 565 | 129 |
| Synthesis Example 10 | 543 | 83 | 583 | 128 | 537 | 133 | 567 | 130 |

Referring to the results of Table 2, each compound according to Synthesis Examples 1 to 10 in a thin film state respectively has a maximum absorption wavelength ($\lambda_{max}$) in a range of 500 nm to 600 nm and a full width at half maximum (FWHM) in a range of 83 nm to 140 nm, and thus shows excellent absorption regarding light in a green wavelength region.

Manufacture of Organic Photoelectric Device

Example 1

An about 150 nm-thick anode is formed by sputtering ITO on a glass substrate, and a 5 nm-thick charge auxiliary layer is formed thereon by codepositing molybdenum oxide ($MoO_x$, $0<x\leq3$) and Al. Subsequently, a 70 nm-thick active layer is formed on the molybdenum oxide ($MoO_x$):Al thin film by codepositing the compound according to Synthesis Example 1 (an n-type semiconductor compound) and Sub-PcCl (a p-type semiconductor compound) in a thickness ratio of 1:1. Subsequently, a 10 nm-thick charge auxiliary layer is formed on the active layer by depositing molybdenum oxide ($MoO_x$, $0<x\leq3$). A 7 nm-thick cathode is formed on the charge auxiliary layer by sputtering ITO, resultantly manufacturing an organic photoelectric device.

Examples 2 to 10

An organic photoelectric device is manufactured according to the same method as Example 1, except for respectively using each compound (an n-type semiconductor compound) according to Synthesis Examples 2 to 10 instead of the compound (an n-type semiconductor compound) according to Synthesis Example 1.

External Quantum Efficiency (EQE)

External quantum efficiency (EQE) of each organic photoelectric device according to Examples 1 to 10 depending on a wavelength and a voltage is evaluated.

The external quantum efficiency is measure by using an IPCE measurement system (McScience Inc., Korea). Firstly, equipment is calibrated by using a Si photodiode (Hamamatsu Photonics K.K., Japan) and mounted with each organic photoelectric device according to Examples 1 to 10, and its external quantum efficiency is measured in a wavelength region ranging about 300 to 700 nm.

Figure 8:
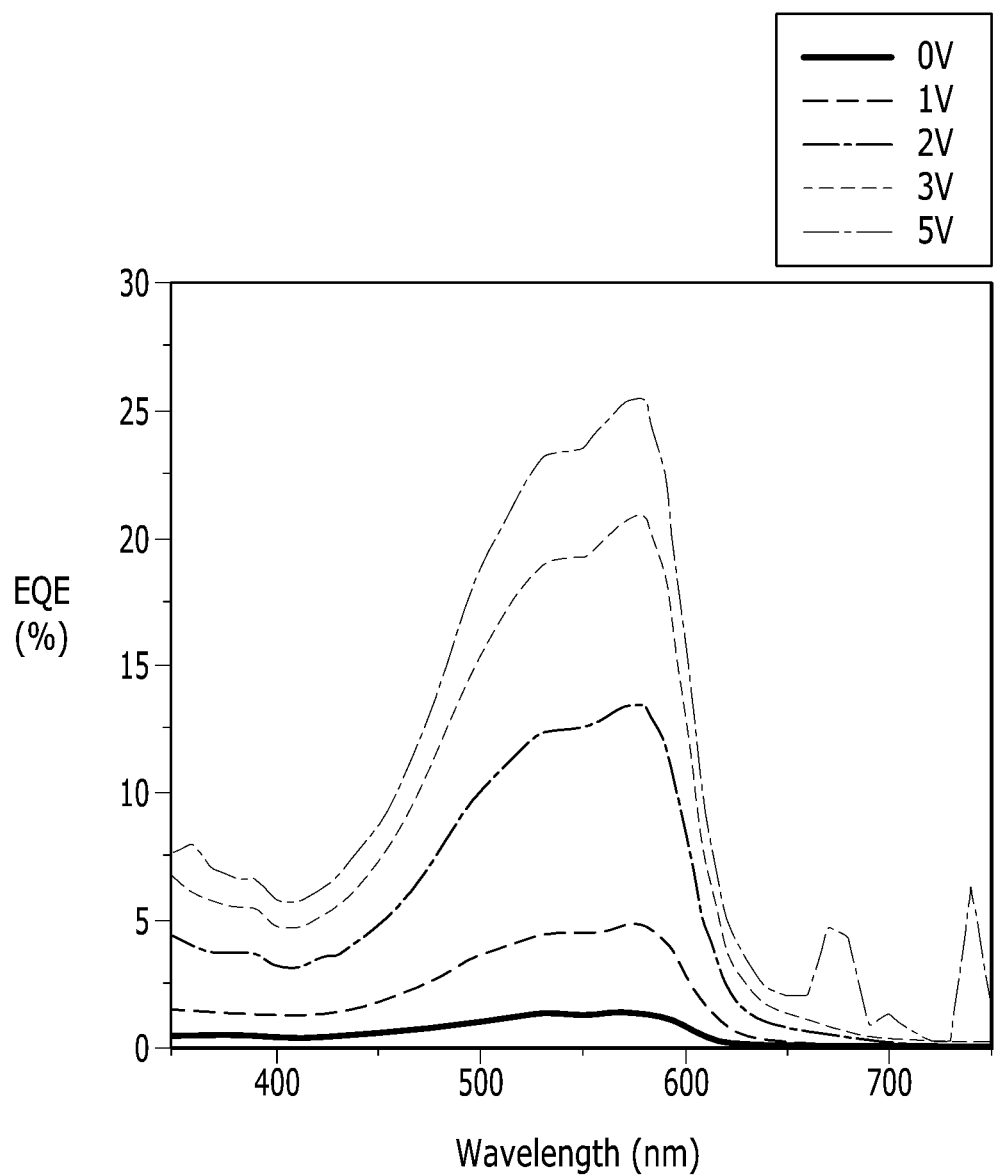
FIG. 8 is a graph showing external quantum efficiency (EQE) depending on a wavelength of the organic photoelectric device according to Example 1.

FIG. 8 shows the external quantum efficiency (EQE) of the organic photoelectric device according to Example 1 depending on a wavelength.

Referring to FIG. 8, the organic photoelectric device according to Example 1 shows satisfactory external quantum efficiency (EQE) in a green wavelength region ranging from about 500 nm to 600 nm.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:
1. An organic photoelectric device comprising:
a first electrode and a second electrode facing each other; and
an active layer between the first electrode and the second electrode, the active layer including an n-type semiconductor compound represented by Chemical Formula 1 and a p-type semiconductor compound having selective light absorption in a green wavelength region of about 500 nm to about 600 nm:

[Chemical Formula 1]

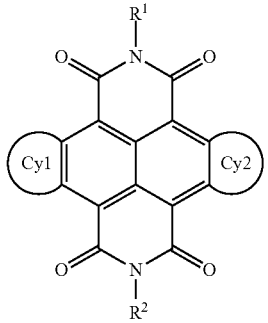

wherein, in Chemical Formula 1,
each of $R^1$ and $R^2$ are independently one of a substituted or unsubstituted $C_1$ to $C_6$ linear or branched alkyl group, a substituted or unsubstituted phenyl group, a substituted or unsubstituted 5-membered to 6-membered heteroaryl group, a substituted or unsubstituted $C_3$ to $C_6$ cycloalkyl group, or a substituted or unsubstituted 3-membered to 6-membered heterocycloalkyl group,
wherein at least one of $R^1$ and $R^2$ is a substituted or unsubstituted phenyl group, a substituted or unsubstituted 5-membered to 6-membered heteroaryl group, a substituted or unsubstituted $C_3$ to $C_6$ cycloalkyl group, or a substituted or unsubstituted 3-membered to 6-membered heterocycloalkyl group, and
each of Cy1 and Cy2 are independently selected from Chemical Formulae 2-1, 2-2, and 2-5:

[Chemical Formulae 2-1]

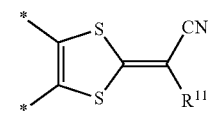

[Chemical Formulae 2-2]

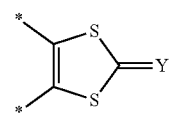

[Chemical Formulae 2-5]

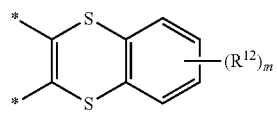

wherein, in Chemical Formula 2-1,
$R^{11}$ is hydrogen, a cyano group (—CN), a carboxyl group (—COOH), an ester group (—COOR, wherein R is a $C_1$ to $C_6$ linear or branched alkyl group), a phenyl group, or a phenyl group substituted with a $C_1$ to $C_6$ alkyl group,
wherein, in Chemical Formula 2-2,
Y is O, S, or NR (wherein R is hydrogen, cyano group, or a $C_1$ to $C_6$ linear or branched alkyl group), and
wherein, in Chemical Formula 2-5, $R^{12}$ is hydrogen, a cyano group, a carboxyl group, or an ester group (—COOR, wherein R is a $C_1$ to $C_6$ linear or branched alkyl group), and m is an integer of 0 to 1.

2. The organic photoelectric device of claim 1, wherein in Chemical Formula 1, Cy1 and Cy2 are the same or different.

3. The organic photoelectric device of claim 1, wherein the n-type semiconductor compound represented by Chemical Formula 1 has 7 to 10 rings.

4. The organic photoelectric device of claim 1, wherein each of the $R^1$ and $R^2$ are independently a $C_1$ to $C_6$ linear or branched alkyl group substituted with cyano group or a halide group, a phenyl group substituted with a cyano group or a halide group, a 5-membered to 6-membered heteroaryl group substituted with a cyano group or a halide group, a $C_3$ to $C_6$ cycloalkyl group substituted with a cyano group or a halide group, or a 3-membered to 6-membered heterocycloalkyl group substituted with a cyano group or a halide group.

5. The organic photoelectric device of claim 1, wherein the p-type semiconductor compound is a compound represented by Chemical Formula 3:

[Chemical Formula 3]

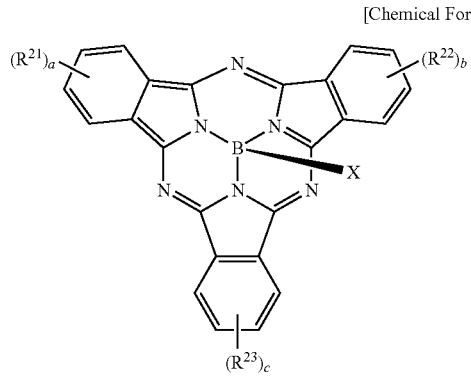

wherein, in Chemical Formula 3, $R^{21}$ to $R^{23}$ are independently hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halide group, a halogen-containing group, or a combination thereof, each of a, b, and c are independently an integer ranging from 1 to 3, and X is a halide group.

6. The organic photoelectric device of claim 5, wherein in Chemical Formula 3, $R^{21}$ to $R^{23}$ are independently a substituted or unsubstituted $C_1$ to $C_{30}$ alkyl group, a substituted or unsubstituted $C_6$ to $C_{30}$ aryl group, or a substituted or unsubstituted $C_3$ to $C_{30}$ heteroaryl group.

7. The organic photoelectric device of claim 1, wherein the p-type semiconductor compound is a compound represented by Chemical Formula 4:

[Chemical Formula 4]

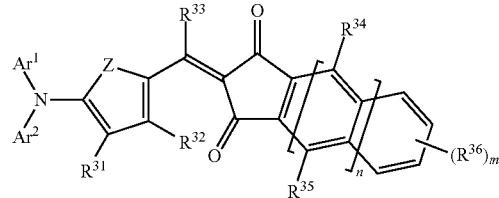

wherein, in Chemical Formula 4,

Z is Se, Te, S(=O), S(=O)$_2$, or SiR$^a$R$^b$ (wherein R$^a$ and R$^b$ are independently hydrogen or a $C_1$ to $C_{10}$ alkyl group), each of Ar$^1$ and Ar$^2$ are independently one of a substituted or unsubstituted $C_6$ to $C_{30}$ aryl group or a substituted or unsubstituted $C_4$ to $C_{30}$ heteroaryl group, each of $R^{31}$ to $R^{36}$ are independently hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, or a halide and cyano group, m is an integer ranging from 0 to 4, and n is 0 or 1.

8. The organic photoelectric device of claim 7, wherein the compound represented by Chemical Formula 4 has 5 to 7 aromatic rings.

9. The organic photoelectric device of claim 7, wherein the Ar$^1$ and Ar$^2$ are a substituted or unsubstituted $C_6$ to $C_{20}$ aryl group.

10. The organic photoelectric device of claim 7, wherein at least one of the Ar$^1$ and Ar$^2$ is a naphthyl group or an anthracenyl group.

11. The organic photoelectric device of claim 1, wherein the active layer has a maximum absorption wavelength ($\lambda_{max}$) of about 500 nm to about 600 nm.

12. The organic photoelectric device of claim 1, wherein the active layer shows a light absorption curve having a full width at half maximum (FWHM) of about 50 nm to about 140 nm.

13. The organic photoelectric device of claim 1, wherein the active layer comprises an intrinsic layer including the n-type semiconductor compound and the p-type semiconductor compound.

14. The organic photoelectric device of claim 13, wherein the active layer further comprises at least one of a p-type layer on one side of the intrinsic layer and an n-type layer on an other side of the intrinsic layer.

15. An image sensor comprising the organic photoelectric device of claim 1.

16. The image sensor of claim 15, further comprising:

a semiconductor substrate integrated with a plurality of first photo-sensing devices configured to sense light in a blue wavelength region and a plurality of second photo-sensing devices configured to sense light in a red wavelength region, wherein the organic photoelectric device is on the semiconductor substrate and selectively absorbs light in a green wavelength region.

17. The image sensor of claim 16, wherein the plurality of first photo-sensing devices and the plurality of second photo-sensing devices are stacked in a vertical direction on the semiconductor substrate.

18. The image sensor of claim 16, further comprising:
a color filter layer between the semiconductor substrate and the organic photoelectric device, the color filter layer including a blue filter configured to selectively absorb light in a blue wavelength region and a red filter configured to selectively absorb light in a red wavelength region.

19. The image sensor of claim 15, wherein
the organic photoelectric device is a green photoelectric device, and
the green photoelectric device, a blue photoelectric device configured to selectively absorb light in a blue wavelength region, and a red photoelectric device configured to selectively absorb light in a red wavelength region are stacked.

20. An electronic device comprising the image sensor of claim 15.

21. An organic photoelectric device comprising:
a first electrode and a second electrode facing each other and
an active layer between the first electrode and the second electrode, the active layer including an n-type semiconductor compound represented by Chemical Formula 1 and a p-type semiconductor compound having selective light absorption in a green wavelength region of about 500 nm to about 600 nm:

[Chemical Formula 1]

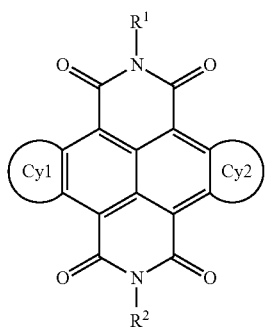

wherein, in Chemical Formula 1,
each of $R^1$ and $R^2$ are independently a substituted or unsubstituted phenyl group, a substituted or unsubstituted 5-membered to 6-membered heteroaryl group, a substituted or unsubstituted $C_3$ to $C_6$ cycloalkyl group, or a substituted or unsubstituted 3-membered to 6-membered heterocycloalkyl group, and
each of Cy1 and Cy2 are independently selected from Chemical Formulae 2-1, 2-2, and 2-5:

[Chemical Formulae 2-1]

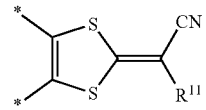

[Chemical Formulae 2-2]

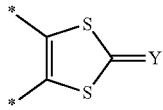

[Chemical Formulae 2-5]

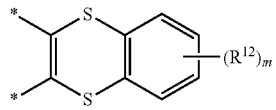

wherein, in Chemical Formula 2-1,
$R^{11}$ is hydrogen, cyano group, a carboxyl group, an ester group (—COOR, wherein R is a $C_1$ to $C_6$ linear or branched alkyl group), a phenyl group, or a phenyl group substituted with a $C_1$ to $C_6$ alkyl group, wherein, in Chemical Formula 2-2,
Y is O, S, or NR (wherein R is hydrogen, cyano group, or a $C_1$ to $C_6$ linear or branched alkyl group), and wherein, in Chemical Formula 2-5,
$R^{12}$ is hydrogen, a cyano group, a carboxyl group, or an ester group (—COOR, wherein R is a $C_1$ to $C_6$ linear or branched alkyl group), and
m is an integer of 0 to 1,
and wherein at least one of Cy1 and Cy2 is Chemical Formula 2-1.

* * * * *